(12) United States Patent
Verkerk et al.

(10) Patent No.: US 12,411,122 B2
(45) Date of Patent: Sep. 9, 2025

(54) SENSITIVITY TRAPS FOR ELECTRONIC TRACE DETECTION HAVING EXPLOSIVES OR NARCOTICS EMBEDDED IN A PLASTICIZED POLYMER MATRIX

(71) Applicant: Rapiscan Systems, Inc., Torrance, CA (US)

(72) Inventors: Udo H. Verkerk, Toronto (CA); Vladimir Romanov, Pelham, NH (US); Hartwig Schmidt, Tewksbury, MA (US); Stefan Lukow, Windham, NH (US); Robert MacRae, Ayer, MA (US); Zachary Andersen, Andover, MA (US)

(73) Assignee: Rapiscan Systems, Inc., Torrance, CA (US)

( * ) Notice: Subject to any disclaimer, the term of this patent is extended or adjusted under 35 U.S.C. 154(b) by 322 days.

(21) Appl. No.: 17/318,917

(22) Filed: May 12, 2021

(65) Prior Publication Data

US 2022/0011286 A1 Jan. 13, 2022

Related U.S. Application Data

(60) Provisional application No. 63/023,368, filed on May 12, 2020.

(51) Int. Cl.
*G01N 33/22* (2006.01)
*G01N 33/15* (2006.01)

(52) U.S. Cl.
CPC .......... *G01N 33/227* (2013.01); *G01N 33/15* (2013.01)

(58) Field of Classification Search
CPC .... G01N 33/15; G01N 33/227; G01N 1/4022; G01N 1/36; G01N 33/0011; G01N 33/0057

(Continued)

(56) References Cited

U.S. PATENT DOCUMENTS 3,067,560 A 12/1962 Frederick
3,186,961 A * 6/1965 Sears .................. C08K 5/0016
528/196

(Continued)

FOREIGN PATENT DOCUMENTS

AT 303589 T 9/2005
AT 480769 T 9/2010

(Continued)

OTHER PUBLICATIONS

Oxlet, J. C. et al, Journal of Energetic Materials 2015, 33, 215-228. (Year: 2015).*

(Continued)

*Primary Examiner* — Arlen Soderquist
(74) *Attorney, Agent, or Firm* — Novel IP

(57) ABSTRACT

Embodiments of the present specification provide methods and systems for sensitivity traps that contain a polymer matrix made from an inert polymer material for encapsulation of trace amounts of explosives and narcotics and a suitable plasticizer material, the types and ratios of which may be selected based on type of analyte that is to be used with the sensitivity trap. The plasticizer material functions by breaking up intra and inter-molecular polymer chain interactions resulting in a larger diffusion coefficient of the analyte within the polymer matrix. Therefore, in embodiments, sufficient amounts of plasticizers are added to the sensitivity trap, which also reduces a glass transition temperature of the polymer matrix and the trap.

27 Claims, 4 Drawing Sheets

(58) Field of Classification Search
USPC .................................................. 436/8
See application file for complete search history.

(56) References Cited

U.S. PATENT DOCUMENTS

| | | | | |
|---|---|---|---|---|
| 3,401,215 | A * | 9/1968 | Evans | C06C 5/04 |
| | | | | 264/3.1 |
| 3,428,502 | A * | 2/1969 | Evans | C06B 45/10 |
| | | | | 149/93 |
| 3,518,943 | A * | 7/1970 | Meers | F42B 1/00 |
| | | | | 102/700 |
| 3,698,316 | A * | 10/1972 | Evans | C06C 5/04 |
| | | | | 149/93 |
| 3,705,480 | A | 12/1972 | Wireman | |
| 3,858,807 | A * | 1/1975 | Rabussier | A01M 1/2044 |
| | | | | 239/57 |
| 4,369,688 | A * | 1/1983 | Yunan | C06B 21/0075 |
| | | | | 264/171.23 |
| 4,699,741 | A * | 10/1987 | Back | C06B 45/22 |
| | | | | 149/93 |
| 4,858,335 | A | 8/1989 | Roth | |
| 4,895,017 | A * | 1/1990 | Pyke | G01N 29/022 |
| | | | | 73/24.06 |
| 5,350,442 | A | 9/1994 | Thelen | |
| 5,359,936 | A * | 11/1994 | Simpson | C06B 23/00 |
| | | | | 102/529 |
| 5,413,812 | A | 5/1995 | Simpson | |
| 5,452,600 | A * | 9/1995 | Davies | G01N 33/0006 |
| | | | | 261/96 |
| 5,491,337 | A | 2/1996 | Jenkins | |
| 5,554,846 | A | 9/1996 | Regiec | |
| 5,600,089 | A * | 2/1997 | Reed, Jr. | C08G 18/4841 |
| | | | | 524/590 |
| 5,624,975 | A * | 4/1997 | Valencia | A61K 9/0024 |
| | | | | 524/145 |
| 5,648,636 | A * | 7/1997 | Simpson | F41H 11/134 |
| | | | | 102/527 |
| 5,719,392 | A | 2/1998 | Franzen | |
| 5,970,804 | A | 10/1999 | Robbat, Jr. | |
| 6,063,365 | A * | 5/2000 | Shefer | A61L 9/048 |
| | | | | 512/1 |
| 6,211,516 | B1 | 4/2001 | Syage | |
| 6,225,623 | B1 | 5/2001 | Turner | |
| 6,247,410 | B1 * | 6/2001 | Garcia | C06B 25/34 |
| | | | | 102/275.9 |
| 6,326,615 | B1 | 12/2001 | Syage | |
| 6,329,653 | B1 | 12/2001 | Syage | |
| 6,382,137 | B1 * | 5/2002 | Derrieu | A01K 27/007 |
| | | | | 119/653 |
| 6,534,765 | B1 | 3/2003 | Robb | |
| 6,568,286 | B1 | 5/2003 | Cabuz | |
| 6,627,444 | B1 * | 9/2003 | Goledzinowski | G01N 27/622 |
| | | | | 250/281 |
| 6,630,664 | B1 | 10/2003 | Syage | |
| 6,642,513 | B1 | 11/2003 | Jenkins | |
| 6,690,005 | B2 | 2/2004 | Jenkins | |
| 6,708,572 | B2 | 3/2004 | Jenkins | |
| 6,737,642 | B2 | 5/2004 | Syage | |
| 6,765,198 | B2 | 7/2004 | Jenkins | |
| 6,815,670 | B2 | 11/2004 | Jenkins | |
| 6,831,273 | B2 | 12/2004 | Jenkins | |
| 6,840,122 | B1 | 1/2005 | Jenkins | |
| 7,014,683 | B2 | 3/2006 | Vierling | |
| 7,047,829 | B2 | 5/2006 | Napoli | |
| 7,109,476 | B2 | 9/2006 | Hanold | |
| 7,119,342 | B2 | 10/2006 | Syage | |
| 7,141,786 | B2 | 11/2006 | McGann | |
| 7,161,144 | B2 | 1/2007 | Syage | |
| 7,196,325 | B2 | 3/2007 | Syage | |
| 7,253,727 | B2 | 8/2007 | Jenkins | |
| 7,299,710 | B2 | 11/2007 | Syage | |
| 7,320,725 | B2 | 1/2008 | Arno | |
| 7,338,638 | B2 | 3/2008 | McGann | |
| 7,361,206 | B1 | 4/2008 | Jahn | |
| 7,401,498 | B2 | 7/2008 | Syage | |
| 7,448,248 | B2 | 11/2008 | Carey | |
| 7,456,393 | B2 | 11/2008 | Napoli | |
| 7,528,367 | B2 | 5/2009 | Haigh | |
| 7,541,577 | B2 | 6/2009 | Davenport | |
| 7,594,422 | B2 | 9/2009 | Perry | |
| 7,594,447 | B2 | 9/2009 | Napoli | |
| 7,663,099 | B2 | 2/2010 | Reda | |
| 7,721,588 | B2 | 5/2010 | Perry | |
| 7,799,567 | B1 | 9/2010 | Call | |
| 7,854,811 | B1 * | 12/2010 | Wartman | C06B 23/00 |
| | | | | 149/93 |
| 7,856,898 | B2 | 12/2010 | Carey | |
| 7,880,137 | B2 | 2/2011 | McGann | |
| 7,932,089 | B2 | 4/2011 | Cohen-Arazi | |
| 8,114,230 | B1 * | 2/2012 | Basom | F42D 5/04 |
| | | | | 149/46 |
| 8,161,830 | B2 | 4/2012 | Boudries | |
| 8,186,234 | B2 | 5/2012 | Syage | |
| 8,288,735 | B2 | 10/2012 | Syage | |
| 8,402,842 | B2 | 3/2013 | Syage | |
| 8,434,375 | B1 | 5/2013 | Syage | |
| 8,614,582 | B2 | 12/2013 | Syage | |
| 8,686,355 | B2 | 4/2014 | Patterson | |
| 8,723,111 | B2 | 5/2014 | Syage | |
| 8,857,278 | B2 | 10/2014 | Syage | |
| 8,866,073 | B2 | 10/2014 | Goedecke | |
| 8,952,327 | B2 | 2/2015 | Patterson | |
| 9,005,524 | B2 | 4/2015 | Deans | |
| 9,147,565 | B1 | 9/2015 | Goedecke | |
| 9,354,153 | B2 | 5/2016 | Syage | |
| 9,482,655 | B2 | 11/2016 | Vilkov | |
| 9,510,780 | B2 | 12/2016 | Silver | |
| 9,528,969 | B2 | 12/2016 | Shaw | |
| 9,558,924 | B2 | 1/2017 | Syage | |
| 9,683,981 | B1 | 6/2017 | Vilkov | |
| 9,689,857 | B1 | 6/2017 | Vilkov | |
| 9,726,655 | B2 | 8/2017 | Syage | |
| 9,766,218 | B2 | 9/2017 | Lai | |
| 9,784,723 | B1 * | 10/2017 | Oxley | G01N 33/227 |
| 9,789,434 | B1 | 10/2017 | Lai | |
| 2003/0164091 | A1 | 9/2003 | Hill | |
| 2003/0165407 | A1 | 9/2003 | Aker | |
| 2004/0089799 | A1 | 5/2004 | Kawato | |
| 2004/0262512 | A1 | 12/2004 | Tobita | |
| 2005/0061964 | A1 | 3/2005 | Nagano | |
| 2005/0089795 | A1 * | 4/2005 | Cole | G03F 7/001 |
| | | | | 430/270.1 |
| 2005/0106380 | A1 * | 5/2005 | Gray | C08J 5/18 |
| | | | | 428/323 |
| 2007/0028670 | A1 | 2/2007 | Bonne | |
| 2007/0221087 | A1 * | 9/2007 | Adebimpe | F42B 8/00 |
| | | | | 102/355 |
| 2007/0281358 | A1 * | 12/2007 | Cohen-Arazi | F42B 8/00 |
| | | | | 436/8 |
| 2008/0131395 | A1 * | 6/2008 | Wellinghoff | A01N 25/10 |
| | | | | 525/55 |
| 2008/0191129 | A1 | 8/2008 | Makarov | |
| 2008/0248578 | A1 | 10/2008 | Deans | |
| 2008/0251599 | A1 * | 10/2008 | Ward | A61L 9/127 |
| | | | | 222/23 |
| 2008/0295783 | A1 * | 12/2008 | Furton | F41H 11/132 |
| | | | | 73/1.01 |
| 2009/0041820 | A1 * | 2/2009 | Wu | A61Q 13/00 |
| | | | | 252/194 |
| 2009/0152458 | A1 | 6/2009 | Vilkov | |
| 2009/0159790 | A1 | 6/2009 | Kostiainen | |
| 2009/0194744 | A1 * | 8/2009 | Adebimpe | F41H 11/134 |
| | | | | 252/408.1 |
| 2011/0272571 | A1 | 11/2011 | Kenttaemaa | |
| 2012/0037797 | A1 | 2/2012 | Li | |
| 2012/0112061 | A1 | 5/2012 | Morokuma | |
| 2014/0191123 | A1 | 7/2014 | Wildgoose | |
| 2014/0264002 | A1 | 9/2014 | Goedecke | |
| 2014/0311218 | A1 * | 10/2014 | Adebimpe | C07D 489/00 |
| | | | | 252/408.1 |
| 2015/0285780 | A1 | 10/2015 | Kelley | |
| 2016/0282304 | A1 | 9/2016 | Vilkov | |

(56) References Cited

U.S. PATENT DOCUMENTS

| | | | |
|---|---|---|---|
| 2016/0341530 A1* | 11/2016 | Hupp | F42B 8/28 |
| 2017/0103880 A1 | 4/2017 | Syage | |
| 2017/0213715 A1 | 7/2017 | Davila | |
| 2017/0261483 A1 | 9/2017 | Vilkov | |
| 2017/0261484 A1 | 9/2017 | Vilkov | |
| 2017/0284977 A1 | 10/2017 | Rogers | |
| 2017/0309463 A1 | 10/2017 | Vilkov | |
| 2018/0158665 A1 | 6/2018 | Eiceman | |
| 2018/0164189 A1 | 6/2018 | Bilodeau | |
| 2018/0172635 A1 | 6/2018 | Lai | |
| 2018/0172650 A1 | 6/2018 | Platow | |
| 2018/0182603 A1* | 6/2018 | Schmidt | G01N 33/0006 |
| 2018/0182604 A1 | 6/2018 | Lai | |
| 2018/0283993 A1 | 10/2018 | Shaw | |
| 2018/0284081 A1 | 10/2018 | Shaw | |
| 2018/0335390 A1 | 11/2018 | Leung | |
| 2018/0339952 A1* | 11/2018 | Brogden | C08K 3/38 |
| 2018/0356320 A1 | 12/2018 | Romanov | |
| 2019/0011421 A1 | 1/2019 | Rogers | |
| 2019/0046974 A1 | 2/2019 | Meketa | |
| 2019/0204274 A1 | 7/2019 | Eiceman | |
| 2019/0228959 A1 | 7/2019 | Verkerk | |

FOREIGN PATENT DOCUMENTS

| | | |
|---|---|---|
| CA | 2153371 C | 3/1999 |
| CA | 2436256 C | 6/2007 |
| CA | 2382823 C | 11/2007 |
| CA | 2362449 C | 10/2008 |
| CA | 2411532 C | 4/2010 |
| CA | 2285153 C | 5/2010 |
| CA | 2479875 C | 2/2011 |
| CA | 2538709 C | 2/2013 |
| CA | 2790430 A1 | 3/2013 |
| CA | 2807894 A1 | 9/2013 |
| CA | 2620405 C | 7/2014 |
| CA | 2548177 C | 9/2014 |
| CA | 2844222 A1 | 9/2014 |
| CA | 2845959 A1 | 9/2014 |
| CA | 2688352 C | 6/2015 |
| CA | 2644937 C | 11/2015 |
| CA | 2904479 A1 | 3/2016 |
| CA | 2910780 A1 | 4/2016 |
| CA | 2913931 A1 | 6/2016 |
| CA | 2915785 A1 | 6/2016 |
| CA | 2924580 A1 | 9/2016 |
| CA | 2647651 C | 11/2016 |
| CA | 2738053 C | 5/2017 |
| CA | 2959791 A1 | 9/2017 |
| CA | 2959796 A1 | 9/2017 |
| CA | 2962154 A1 | 9/2017 |
| CA | 2964147 A1 | 10/2017 |
| CN | 101093211 A | 12/2007 |
| CN | 101120247 A | 2/2008 |
| CN | 100445767 C | 12/2008 |
| CN | 101600960 A | 12/2009 |
| CN | 103308590 A | 9/2013 |
| CN | 103367092 A | 10/2013 |
| CN | 103650102 A | 3/2014 |
| CN | 105738461 A | 7/2016 |
| CN | 107037114 A | 8/2017 |
| CN | 107167334 A | 9/2017 |
| CN | 107167335 A | 9/2017 |
| CN | 107271254 A | 10/2017 |
| CN | 109270156 A | 1/2019 |
| DE | 69528418 T2 | 1/2003 |
| DE | 69926965 T2 | 6/2006 |
| EP | 1048540 A1 | 11/2000 |
| EP | 1517129 A2 | 3/2005 |
| EP | 2368102 A2 | 9/2011 |
| EP | 2587259 A1 | 5/2013 |
| EP | 2637013 A2 | 9/2013 |
| EP | 2778650 A2 | 9/2014 |
| EP | 2778669 A1 | 9/2014 |
| EP | 2884254 A1 | 6/2015 |
| EP | 3015858 A1 | 5/2016 |
| EP | 3032570 A2 | 6/2016 |
| EP | 3040717 A1 | 7/2016 |
| EP | 1938078 B1 | 3/2017 |
| EP | 1297554 B1 | 4/2017 |
| EP | 3182111 A1 | 6/2017 |
| ES | 2183855 | 4/2003 |
| FR | 692712 A | 11/1930 |
| GB | 992782 A | 5/1965 |
| GB | 2075578 A | 11/1981 |
| GB | 2496286 A | 5/2013 |
| GB | 2536076 A | 9/2016 |
| JP | 3045655 B2 | 5/2000 |
| JP | 2006064325 | 3/2006 |
| WO | 0209847 A2 | 2/2002 |
| WO | 2008060666 A2 | 5/2008 |
| WO | 2009023361 A2 | 2/2009 |
| WO | WO-2017141201 A1 * | 8/2017 |

OTHER PUBLICATIONS

Oxley, J. C. et al, Journal of Energetic Materials 2015, 33, 215-228. (Year: 2015).*

Perreault, L. J., Thesis 2017, 67 pages. (Year: 2017).*

International Search Report for PCT/US2021/032059, Sep. 15, 2021.

Cody et al., "Versatile New Ion Source for the Analysis of Materials in Open Air under Ambient Conditions", Anal. Chem., 2005, vol. 77, pp. 2297-2302.

* cited by examiner

| Analyte | 0 Wt% | 4 Wt% | 14 Wt% | 24 Wt% | % Rate Change (0 to 14 Wt%) |
|---|---|---|---|---|---|
| TNT | 4503 [8.0E-11] | 6847 [2.6E-10] | 5476 [4.2E-10] | 7278 [3.4E-10] | 22 |
| RDX | 1459 [] | 2357 [] | 1930 [] | 1529 [] | 32 |
| PETN | 1191 [1.1E-10] | 1529 [2.8E-10] | 1983 [5.4E-10] | 1744 [4.8E-10] | 67 |

Analyte release rate (au/sec) and [diffusion coefficient] (cm2/sec) as a function of Wt% DIOP plasticizer in Polycarbonate

FIG. 4

SENSITIVITY TRAPS FOR ELECTRONIC TRACE DETECTION HAVING EXPLOSIVES OR NARCOTICS EMBEDDED IN A PLASTICIZED POLYMER MATRIX

CROSS-REFERENCE

The present application relies on U.S. Patent Provisional Application No. 63/023,368 (the "'368 Application"), entitled "Sensitivity Traps for Electronic Trace Detection" and filed on May 12, 2020, for priority. The '368 Application is hereby incorporated herein by reference.

FIELD

The present specification relates to improved sensitivity traps used to calibrate and/or verify the functionality, precision and/or accuracy of Electronic Trace Detectors (ETD).

BACKGROUND

Electronic Trace Detectors (ETDs) employ a thermal source that is used to vaporize one or more substances (e.g., a sample, calibrant, verification substance, and/or sensitivity substance) within the detector. Those substances are located on, or encapsulated within, a device referred to as a trap. The vaporized substances are then directed via controlled air flows to one or more detectors. ETDs typically use sensitivity traps with a relatively large amount of substances to ensure continued accuracy of measurements. There is a need, however, for sensitivity traps that contain a much smaller quantity of substances in order to cover the lower detection range of the ETD. Such a sensitivity trap would still enable a reliable assessment of the performance and sensitivity of the detection instruments on a regular basis, have a long shelf life, resist high humidity and temperatures but would do so with far less dangerous material while allowing ease of adaptation for different vaporization conditions.

Some of the currently known sensitivity traps contain smaller quantities of substances such as explosive materials and narcotic materials and are formed by adsorption on or encapsulation by an inert polymer material. The traps created by these processes do not have a sufficiently sharp desorption profile or a long shelf life and cannot easily be adapted for different vaporization conditions.

U.S. Pat. No. 5,359,936, assigned to Regents of the University of California, discloses "use of standard slurry coatings to produce a material with a very high binder to explosive ratio without masking the explosive vapor, and coating inert beads with thin layers of explosive molecules".

U.S. Pat. No. 6,627,444, assigned to Smiths Detection, discloses "Filter discs or other suitable substrates are impregnated, by the process of adsorption, with solutions of known concentrations of analytes and chromatographic phase materials, such as polymers, in suitable solvents. The substrate material is selected to be chemically inert and to not negatively interact with the analytes, the calibration process, or the analytical instrumentation. The polymers cause the analyte to adhere to the substrate until the solution is desorbed by heating, so that the impregnated substrates form stable calibration solutions in solid phase which can be easily and reliably stored, transported, and used by operators with minimal training. The substrate is preferably contained in a card holder which can be easily inserted into and preferably mate with an inlet for the analytical instrument. Within the instrument, the solid phase calibrant is desorbed by heating the substrate to release a standardized amount of analyte calibrant into the instrument."

U.S. Pat. No. 7,932,089, assigned to Rafael Armament Development Authority Ltd., discloses "simulant material includes a quantity of at least one explosive material and at least one inert material. The simulant material is a non-explosive material and is in the form of a homogenous, flexible and non-particulated material."

U.S. Pat. No. 9,784,723, assigned to Board of Governors for Higher Education, State of Rhode Island and Providence Plantations, discloses "a non-detonable explosive vapor sources consisting of an explosive (at the 5 to 50%) encapsulated in a polymer which retains the explosive vapor until heat is applied. The invention utilizes plastic microspheres or microcapsules that contain an amount of the actual explosive or the elements of the characteristic explosive headspace (vapor) signature. The actual explosive is encased in a shell material of plastic, either in microcapsules or microspheres."

None of these methods and systems provide for a sufficiently sharp thermal desorption profile, cannot easily be adapted for different temperature profiles and are unable to effectively minimize the amounts of explosive and narcotic material that need to be carried by the polymer. Accordingly, there is still a need for methods and systems that permit the use of low level dosing of explosives and narcotics to be used to accurately assess fielded systems for sensitivity. There is also a need for a polymer-based containment of explosive and narcotic materials that, at the operating temperature of the thermal source, provide sufficient mobility for the analyte contained in the polymer matrix. There is also a need for improved sensitivity traps that could also be used to assess detection units before they are shipped to users.

SUMMARY

The following embodiments and aspects thereof are described and illustrated in conjunction with systems, tools and methods, which are meant to be exemplary and illustrative, not limiting in scope.

The present specification discloses a method of manufacturing a sensitivity trap, wherein the sensitivity trap comprises a polymer matrix and at least one analyte embedded within the polymer matrix, and wherein the sensitivity trap is defined by a target glass transition temperature, the method comprising: selecting an amount and a type of plasticizer, wherein the amount and the type of the plasticizer is based upon a type of the at least one analyte and at least one of the target glass transition temperature or a diffusion coefficient of the at least one analyte; dissolving a polymer and the selected amount and type of plasticizer in a solvent to form a mixture; adding the at least one analyte to the mixture; and removing the solvent from the mixture to obtain the sensitivity trap.

Optionally, the method further comprises depositing a predefined amount of the mixture on a surface.

Optionally, the at least one analyte comprises at least one of an explosive material, a narcotic material, or a combination of an explosive and a narcotic material.

Optionally, an amount of the at least one analyte in the polymer matrix is less than 100 nanograms.

Optionally, the at least one analyte comprises at least one of a nitroaromatic composition, a nitramine composition, a nitro-ester composition, a nitrate composition, or a peroxide composition.

Optionally, the polymer is a polycarbonate composition.

Optionally, the method further comprises adjusting the target glass transition temperature.

Optionally, the plasticizer is diisooctyl phthalate.

Optionally, the target glass transition temperature is in a range of −30 to 140 degrees Celsius.

Optionally, the method further comprises determining a rate of release of the analyte from the sensitivity trap by adjusting the amount and type of the plasticizer.

Optionally, the polymer is a polycarbonate composition and wherein the plasticizer is diisooctyl phthalate.

Optionally, the amount of the plasticizer is between 4 and 24 $W_t$ percent.

Optionally, the amount of the plasticizer is approximately 14 $W_t$ percent.

Optionally, the plasticizer is at least one of tributyl citrate, acetyl triethyl citrate, diisooctyl phthalate, or triisononyl trimellitate.

Optionally, the polymer is at least one of an inert organic polymer material, polystyrene, polycarbonate, and polylactic-co-glycolic acid.

In some embodiments, the present specification describes a sensitivity trap defined by a target glass transition temperature, comprising: a polymer matrix; at least one analyte embedded within the polymer matrix; and a plasticizer, wherein an amount and a type of the plasticizer is based upon the target glass transition temperature and a type of the at least one analyte.

Optionally, the at least one analyte comprises at least one of an explosive material, a narcotic material, or a combination of an explosive and a narcotic material.

Optionally, an amount of the at least one analyte in the polymer matrix is less than 100 nanogram in a solvent-cast membrane.

Optionally, the explosive material comprises at least one of a nitroaromatic composition, a nitramine composition, a nitro-ester composition, a nitrate composition, or a peroxide composition.

Optionally, the polymer is a polycarbonate composition and wherein the plasticizer is diisooctyl phthalate.

Optionally, the amount of the plasticizer is between 4 and 24 $W_t$ percent.

Optionally, the amount of the plasticizer is approximately 14 $W_t$ percent.

Optionally, the glass transition temperature is in a range of −30 to 140 degrees Celsius.

Optionally, the plasticizer is at least one of tributyl citrate, acetyl triethyl citrate, diisooctyl phthalate, or triisononyl trimellitate.

Optionally, the polymer is at least one of an inert organic polymer material, polystyrene, polycarbonate, or polylactic-co-glycolic acid.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 4 shows desorption rates and diffusion coefficients for different materials in relation to different polymer-plasticizer ratios, in accordance with some embodiments of the present specification.

DETAILED DESCRIPTION

Figure 1:
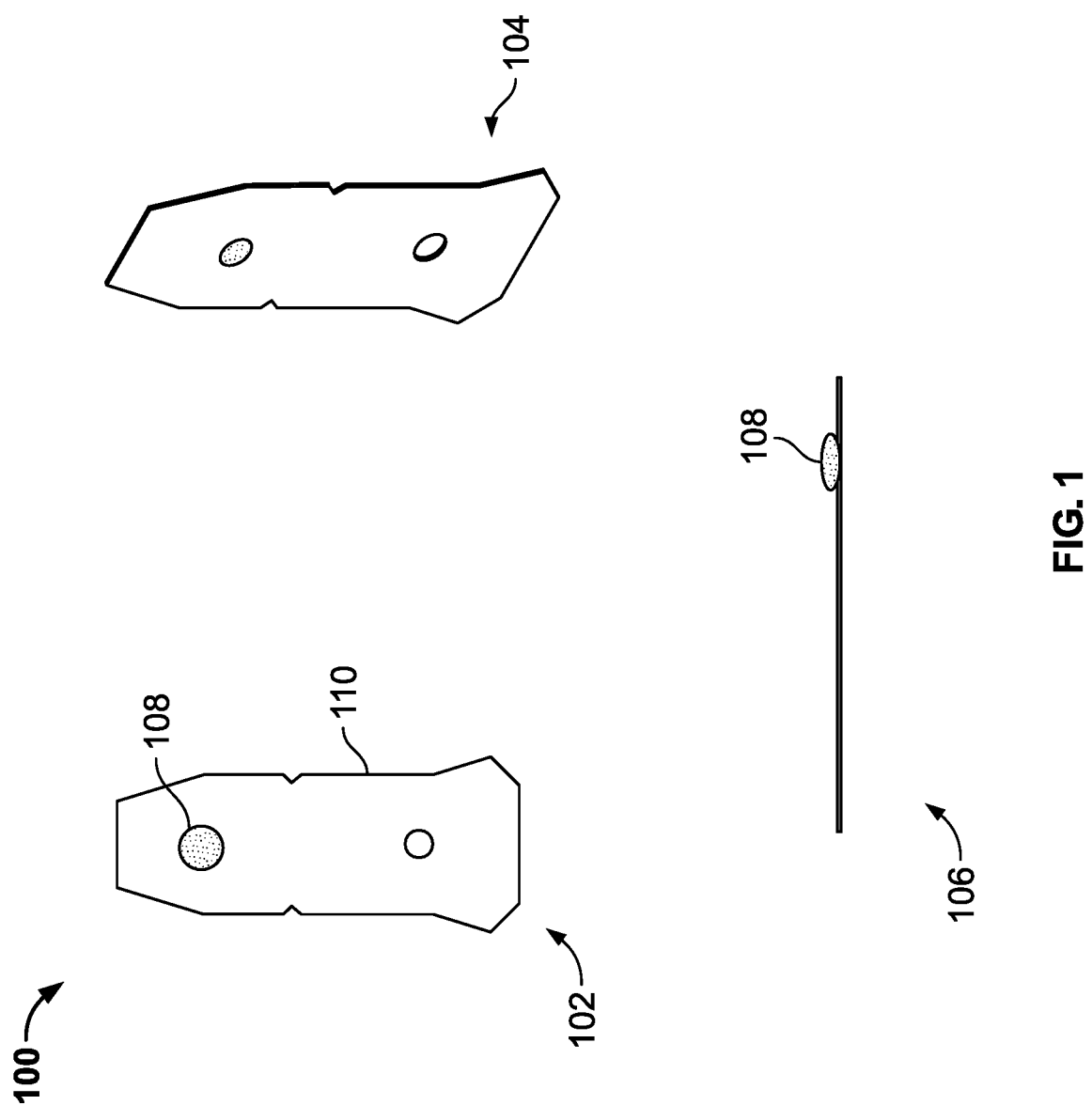
FIG. 1 shows a schematic of an exemplary trap, in accordance with some embodiments of the present specification.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present specification.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

One of ordinary skill in the art would understand that the specific traps disclosed herein are configured to be used in electronic trace detectors employing a thermal source. The thermal source employing a constant or ramped temperature profile, for example between room temperature to 250° C., is used to vaporize one or more substances located on, or encapsulated within, a trap. The vaporized substances are carried by air flow to one or more detectors. In some embodiments, the detector (also referred to herein as an "analysis device") includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (MIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a mass spectrometer (MS), a gas chromatograph (GC), or combinations thereof. The detector is configured to detect and identify constituents in a sample input thereto. For example, the detector is configured to detect one or more substances of interest in a sample trap, such as one or more volatile or non-volatile substances of interest like explosives and narcotics.

In embodiments, the system further includes a computing device. In some embodiments, the computing device may be located remote from the system. In some other embodiments, the computing device is integral to system. In some embodiments, the computing device includes a memory device and a processor operatively coupled to the memory device for executing instructions. In some embodiments, executable instructions are stored in the memory device. Computing device is configurable to perform one or more operations described herein by the programming processor. For example, in some embodiments, the processor is programmed by encoding an operation as one or more executable instructions and providing the executable instructions in the memory device. In the exemplary embodiment, the memory device is one or more devices that enable storage and retrieval of information such as executable instructions and/or other data. The memory device includes one or more computer readable media in some embodiments.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

The memory device is configured to store a pre-programmed library of mobility spectra, each mobility spectrum associated with one substance of a plurality of substances. The memory device may further store associated drift times, alarm limits, detection history, calibration profiles and history (e.g., verification history) for the detector, and/or any other type of data in some embodiments. In the exemplary embodiment, the computing device, including the memory device, includes, without limitation, sufficient computer-readable/executable instructions, sufficient data and data structures, algorithms, and commands to facilitate detection of substance(s) introduced into the detector (e.g., a sample, the calibrant, the verification substance, and/or the sensitivity substance).

To ensure the accurate operation of the electronic trace detectors, it is important to test them periodically to make sure they are properly detecting a known amount of certain materials. As previously explained, however, conventional traps used to test the lower range of sensitivity and/or accuracy of an ETD suffer from requiring excessive quantities of analyte materials. These conventional sensitivity traps have a short shelf life, low resistivity to humidity and/or an insufficiently sharp desorption profile and cannot be easily adapted for different thermal desorption profiles.

Embodiments of the present specification provide methods and systems for sensitivity traps that contain a polymer matrix made from an inert polymer material for encapsulation of trace amounts of analyte materials, for instance explosives and narcotics. A polymer matrix is defined as a plurality of short and/or long fibers, made of polymer material, that are organized in grid, crossing, or skew configuration such that a load is transferred and spread among the fibers.

The sensitivity traps, depicted in FIG. 1, of the present specification have a long shelf life and can easily be adapted for different thermal desorption profiles by using a combination of an inert plasticizer material and an inert organic polymer material. The plasticizer material is added to increase the mobility of an analyte within the polymer matrix at the operating temperature of the thermal source, thereby adding to the room temperature shelf life of the sensitivity trap and improving the thermal desorption profile. The function of the plasticizer material is to break up intra and inter-molecular polymer chain interactions lowering the glass transition temperature ($T_g$) of the polymer matrix. This allows for greater movement of the analyte within the polymer matrix resulting in the desired increase in the diffusion coefficient (D) of the analyte. Therefore, in embodiments, sufficient amounts of plasticizers are added to the sensitivity trap to reduce the polymer $T_g$ and increase the diffusion coefficient D. In some embodiments, the $T_g$ is reduced below ambient temperature.

In embodiments, the rate of transport of analytes from the bulk of the polymer matrix to the polymer-air interface is enhanced by the use of plasticizers by increasing the diffusion coefficient of the analytes. As a result the evaporation of the explosives and narcotics from the polymer matrix in the sensitivity traps is not limited by analyte surface depletion and is therefore more efficient. The plasticizer/polymer weight ratio determines the polymer matrix $T_g$. Adjustment of this ratio therefore changes the polymer matrix $T_g$, the diffusion coefficient D and rate of transport of the analyte towards the polymer-air interface to allow for a sharp thermal desorption profile. In cases when no plasticizer material is present in the solvent-cast membrane it may take additional time during the temperature ramp of the desorber to reach and surpass the polymer $T_g$ in order to release the explosives. The delay in releasing the explosive material is measurable and may be in the order of seconds.

Figure 2:
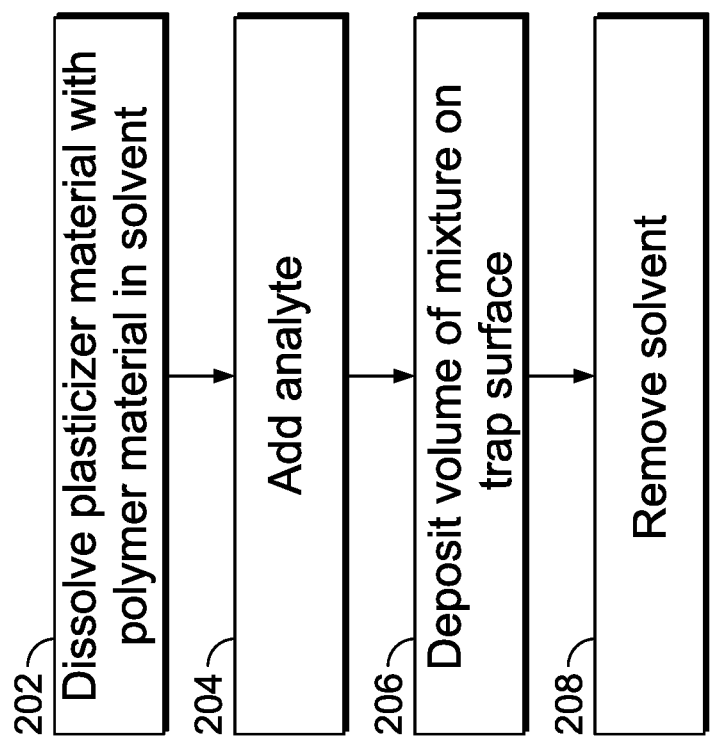
FIG. 2 is a flowchart depicting a method of manufacturing exemplary traps, in accordance with some embodiments of the present specification.

FIG. 2 is a flow chart illustrating an exemplary process of manufacturing the trap in accordance with the embodiments of the present specification. In embodiments, at 202, the trap in accordance with the present specification is manufactured by dissolving a plasticizer material with a polymer material in a preferably volatile solvent, for example tetrahydrofuran, acetone, methanol, dichloromethane, toluene, xylene or mixtures of these. In embodiments, the amount of plasticizer added is based on the desired mobility and rate of release of an analyte from within the polymer matrix at the desorber operating temperature.

At 204, an analyte is added to the solution of the plasticizer and polymer. Subsequently at 206, a volume of this solution, for example in a range of 1 to 100 microliters or any increment therein such as 10 microliters, is deposited on the surface of a carrier to form the trap. The carrier is an inert material under the trap heating conditions, for example a metal, glass or ceramic material. Evaporation of the solvent at 208 results in a solvent-cast membrane with a radius in a range of 0.5 to 4 mm, any increment between 0.5 to 4 mm, and most preferably between 1.5 and 2.2 mm on top of the trap material as depicted in FIG. 1. The analyte may be an explosive, narcotic or any other substance, or mixtures of these. A person of ordinary skill in the art will understand that the plasticizer weight percentage required to obtain a specific explosive diffusion coefficient and polymer matrix $T_g$ is a function of the explosive and polymer-plasticizer combination, respectively. For purposes of this description, the remaining details are provided with reference to use of a single explosive in a single polymer-plasticizer combination.

In embodiments, the amount of explosive material added to the solution of the plasticizer material and the polymer material is less than 5% $W_t$ (percentage by weight), preferably less than 2.5% $W_t$, and more preferably less than 1% $W_t$ (percentage by weight). Therefore, the amount of explosive material is maintained at a low level.

The polymer material used is an inert organic polymer material. Examples of polymer materials used may include, but are not limited to, polystyrene, polycarbonate and/or PLGA (poly(lactic-co-glycolic acid)).

Acceptable plasticizers are characterized by a combination of a very low vapor pressure at the upper operating temperature range of a desorber, and compatibility with the casting solvent and polymer employed. Examples of acceptable plasticizer materials may include, but are not limited to, tributyl citrate (6E-7 mm Hg, 25° C.), acetyl triethyl citrate (2E-4 mm Hg, 25° C.), diisooctyl phthalate (2E-8 mm Hg, 25° C.), and/or triisononyl trimellitate (<0.1 mm Hg, 200° C.). In an example, polystyrene, (molecular weight 190000 gr/mol, $T_g$ of 89° C.) may be combined with tributyl citrate in $W_t$ percentages of 9, 17, and 29 using xylene as solvent to yield a $T_g$ of 65, 55 and 34° C. respectively for the plasticized polymer matrix after evaporation of the solvent. In another example, polylactic acid (molecular weight 137000 gr/mol, $T_g$ of 59° C.) may be combined with acetyl triethyl citrate in $W_t$ % of 10, 20, 30 using dichloromethane as solvent, to yield a $T_g$ of 51, 30 and 14° C. respectively for the plasticized polymer matrix after removal of the solvent. For a sharp, accelerated analyte desorption profile a low Tg is preferred. Using for example polystyrene and tributyl citrate as plasticizer, a plasticizer $W_t$ percentage equal to or above 17% is desirable. For a slow, delayed analyte desorption profile a high Tg is preferred. Using for example polylactic acid and acetyl triethyl citrate as plasticizer, a plasticizer $W_t$ percentage equal to or below 10% is desirable.

Examples of the explosive material used may include, but are not limited to, nitroaromatic, nitramine, nitro ester, nitrate, and/or peroxide. In embodiments, based on the type of the explosive material, its concentration in the solvent-cast membrane may be as low as 1 nanograms (ng) and up to 100 ng. Examples of the given range of concentration may also be applicable to other types of analytes such as narcotics or combinations of narcotics and explosives. Using the various combinations of plasticizer materials and polymer materials and concentration of explosives in the solvent-cast membrane that are within 100 ng, the shelf life of the resulting trap may be at least six months when stored in temperatures up to 45° C. The explosive material may be added as a solid, as a solution, or as a dispersion in the same or a different solvent.

The solvent cast-membrane, after removal of the solvent, may be a homogeneous or heterogeneous material with regard to the dispersion of the explosive in the membrane. The membrane's properties are determined by the plasticizer material properties, the polymer material properties and the weight ratio of these. The membrane material at room temperature may be anywhere between a hard solid to a flexible material.

Figure 3:
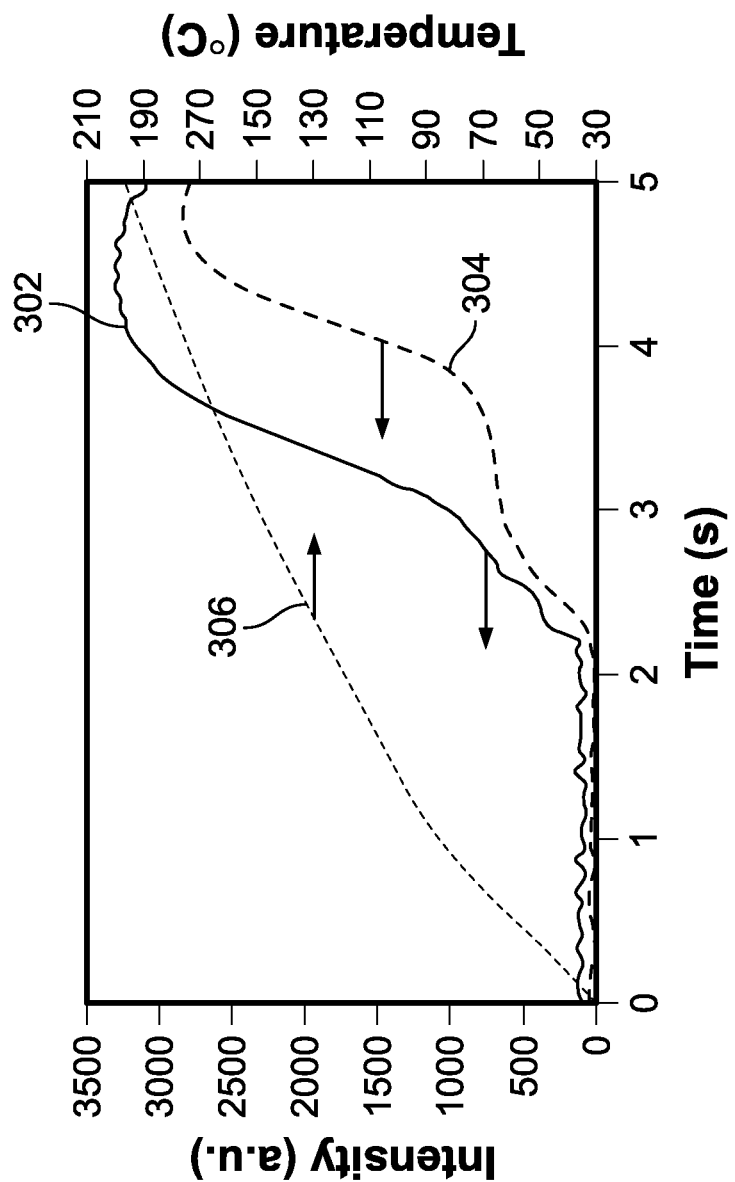
FIG. 3 shows desorption profiles of exemplary traps, in accordance with some embodiments of the present specification.

FIG. 3 illustrates an exemplary graph and comparison of analyte desorption as a function of time and desorber temperature (desorption profile) of a sensitivity trap with and without a plasticizer material using a PETN type of explosive material in accordance with some embodiments of the present specification. Referring to the graph, a plot 306 is a temperature profile of the sensitivity trap as a function of time. A plot 302 is a PETN desorption profile as a function of time for a polymer matrix that uses a plasticizer material, specifically a combination of polycarbonate (PC) and diisooctyl phthalate (DIOP). A plot 304 is a PETN desorption profile as a function of time for a polymer matrix that does not use any plasticizer material, and includes only polycarbonate. As seen in the graph, the polymer matrix containing the plasticizer (plot 302) results in a much more rapid and defined onset of the release of PETN at a lower temperature. In absence of the plasticizer (plot 304) a step is present in the desorption profile resulting in a delay in the PETN desorption. While FIG. 3 illustrates the plot for PETN type of explosive material, the plots for different explosive materials may vary. Accordingly, suitable combinations of polymer and plasticizer for different explosive materials may be used to obtain desorption profiles with an adjustable onset of explosive release. For example, a typical IMS trace detector only has a limited time window of approximately 3 to 4 seconds available for the explosive desorption off the sensitivity trap into the detector. A sensitivity trap may therefore fail to release the analyte at the desired trace level within the required time. Therefore, it is desirable to be able to adjust the timing of the explosive release, which is facilitated by the embodiments of the present specification.

Accordingly, in one embodiment, the desorption profile as a function of time for a polymer matrix that uses a plasticizer material, as described herein, achieves a 1000 (a.u.) level of intensity within less than 3 seconds, and preferably in a range of 2-3 seconds. In one embodiment, the desorption profile as a function of time for a polymer matrix that uses a plasticizer material, as described herein, achieves a 3000 (a.u.) level of intensity within less than 4 seconds, and preferably in a range of 3-4 seconds. In one embodiment, the desorption profile as a function of time for a polymer matrix that uses a plasticizer material, as described herein, achieves a 3000 (a.u.) level of intensity within less than 4 seconds and at a temperature of less than 200 degrees Celsius. In one embodiment, the desorption profile as a function of time for a polymer matrix that uses a plasticizer material, as described herein, achieves a 2000 (a.u.) level of intensity within less than 4 seconds (preferably in a range of 3-4 seconds) and at a temperature of less than 150 degrees Celsius.

FIG. 4 illustrates an exemplary table listing the release rates and diffusion coefficients of different explosives 402 for different constituents 404 of a sensitivity trap, in accordance with some embodiments of the present specification. Referring to the table, a column 406 lists the release rate of explosives 402 measured over a 3 second time window beginning at the heating of the trap. In FIG. 4 the diffusion coefficients for the different explosives 402 are supplied in square brackets. Column 406 lists the release rate when only a polymer material (polycarbonate (PC)) is used to constitute the sensitivity trap. Another column 408 lists the release rate for the same explosives 402 with a combination of a polymer (polycarbonate (PC)) and a plasticizer (diisooctyl phthalate (DIOP)). Comparison between values of columns 406 and 408 indicates that the release rate is higher for column 408, reflecting an early onset of explosive release as a result of the increase of the diffusion coefficient of the explosives 402. A percentage rate change for each explosive is also listed in a column 410. For PETN, the difference in the mass release of the explosive without and with plasticizer is 67%. Different columns in the table also indicate that an optimal release rate is achieved with about 14 $W_t$ % of plasticizer material, relative to less (4 $W_t$ %) or more (24 $W_t$ %) of the plasticizer for this plasticizer/polymer combination. The release rate may increase or decrease with an increase in the amount of the plasticizer, based on the type of explosive, polymer and plasticizer. Accordingly, in one embodiment, using PC an amount of the DIOP plasticizer ranges from about 4 to about 24 Wt %.

Embodiments of the present specification enable manufacturing of sensitivity traps with low concentrations of explosives or other analytes, in the polymer matrix. The selective addition of plasticizer material to the polymer matrix enables modification of the diffusion coefficient D of the analytes incorporated in the polymer matrix. Lowering of the $T_g$ of the polymer matrix increases the diffusion coefficient D for adjustment of the onset of analyte release and increases the shelf life of the sensitivity trap. The low dosing of explosives and narcotics, in accordance with the embodiments of the present specification, permits accurate assessment of field detection systems for sensitivity.

Although specific features of various embodiments of the disclosure may be shown in some drawings and not in others, this is for convenience only. In accordance with the principles of the disclosure, any feature of a drawing may be referenced and/or claimed in combination with any feature of any other drawing. The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of manufacturing a sensitivity trap, wherein the sensitivity trap comprises a polymer matrix made of a polymer material, and at least one analyte embedded within the polymer matrix, and wherein the sensitivity trap is defined by a target glass transition temperature, the method comprising:
   selecting an amount and a type of plasticizer, wherein the amount and the type of the plasticizer is based upon a type of the at least one analyte and at least one of the target glass transition temperature or a diffusion coefficient of the at least one analyte and wherein said amount of plasticizer is sufficient to increase a diffusion coefficient of the at least one analyte such that, when the sensitivity trap is inserted into an ion mobility spectrometer (IMS) and exposed to a heating rate of approximately 33° C. per second, the at least one analyte is released from the mixture with sufficient desorption intensity to reach at least 2000 a.u. as measured by the IMS within 4 seconds of initiating heating;
   dissolving a polymer and the selected amount and type of plasticizer in a solvent to form a mixture;
   adding the at least one analyte to the mixture;
   removing the solvent from the mixture; and
   depositing the mixture onto a carrier to form the sensitivity trap.

2. The method of claim 1, further comprising depositing a predefined amount of the mixture on a surface.

3. The method of claim 1, wherein the at least one analyte comprises at least one of an explosive material, a narcotic material, or a combination of an explosive and a narcotic material.

4. The method of claim 1, wherein an amount of the at least one analyte in the polymer matrix is less than 100 nanograms.

5. The method of claim 1, wherein the at least one analyte comprises at least one of a nitroaromatic composition, a nitramine composition, a nitro-ester composition, a nitrate composition, or a peroxide composition.

6. The method of claim 1, wherein the polymer is a polycarbonate composition.

7. The method of claim 6, further comprising adjusting the target glass transition temperature.

8. The method of claim 7, wherein the plasticizer is diisooctyl phthalate.

9. The method of claim 8, wherein the target glass transition temperature is in a range of −30 to 140 degrees Celsius.

10. The method of claim 1, further comprising determining a rate of release of the analyte from the sensitivity trap by adjusting the amount and type of the plasticizer.

11. The method of claim 1, wherein the polymer material is a polycarbonate composition and wherein the plasticizer is diisooctyl phthalate.

12. The method of claim 11, wherein the amount of the plasticizer is between 4 and 24 $W_t$ percent.

13. The method of claim 11, wherein the amount of the plasticizer is approximately 14 $W_t$ percent.

14. The method of claim 1, wherein the plasticizer is at least one of tributyl citrate, acetyl triethyl citrate, diisooctyl phthalate, or triisononyl trimellitate.

15. The method of claim 1, wherein the polymer material is at least one of an inert organic polymer material, polystyrene, polycarbonate, or polylactic-co-glycolic acid.

16. The method of claim 1, wherein the carrier comprises at least one of metal, glass and ceramic material.

17. A sensitivity trap defined by a target glass transition temperature, comprising:
   a polymer matrix made of a polymer material;
   at least one analyte embedded within the polymer matrix;
   a plasticizer, wherein an amount and a type of the plasticizer is based upon the target glass transition temperature and a type of the at least one analyte and wherein said amount of plasticizer is sufficient to increase a diffusion coefficient of the at least one analyte such that, when the sensitivity trap is inserted into an ion mobility spectrometer (IMS) and exposed to a heating rate of approximately 33° C. per second, the at least one analyte is released from the mixture with sufficient desorption intensity to reach at least 2000 a.u. as measured by the IMS within 4 seconds of the onset of heating; and
   a carrier material upon which the polymer matrix, at least one analyte, and plasticizer are deposited.

18. The sensitivity trap of claim 17, wherein the at least one analyte comprises at least one of an explosive material, a narcotic material, or a combination of an explosive and a narcotic material.

19. The sensitivity trap of claim 18, wherein the explosive material comprises at least one of a nitroaromatic composition, a nitramine composition, a nitro-ester composition, a nitrate composition, or a peroxide composition.

20. The sensitivity trap of claim 17, wherein an amount of the at least one analyte in the polymer matrix is less than 100 nanogram in a solvent-cast membrane.

21. The sensitivity trap of claim 17, wherein the polymer material is a polycarbonate composition and wherein the plasticizer is diisooctyl phthalate.

22. The sensitivity trap of claim 21, wherein the amount of the plasticizer is between 4 and 24 $W_t$ percent.

23. The sensitivity trap of claim 21, wherein the amount of the plasticizer is approximately 14 $W_t$ percent.

24. The sensitivity trap of claim 21, wherein the glass transition temperature is in a range of −30 to 140 degrees Celsius.

25. The sensitivity trap of claim 17, wherein the plasticizer is at least one of tributyl citrate, acetyl triethyl citrate, diisooctyl phthalate, or triisononyl trimellitate.

26. The sensitivity trap of claim 17, wherein the polymer material is at least one of an inert organic polymer material, polystyrene, polycarbonate, or polylactic-co-glycolic acid.

27. The sensitivity trap of claim 17, wherein the carrier material is at least one of metal, glass and ceramic.

\* \* \* \* \*